United States Patent [19]

Nebuloni

[11] Patent Number: 4,726,683
[45] Date of Patent: Feb. 23, 1988

[54] COUPLING BETWEEN ENTRAINING HUB AND MULTI-CUVETTE ROTOR FOR ANALYTICAL APPARATUS

[75] Inventor: Luigi Nebuloni, Ossona, Italy
[73] Assignee: Instrumentation Laboratory S.p.A., Milan, Italy
[21] Appl. No.: 942,867
[22] Filed: Dec. 17, 1986
[30] Foreign Application Priority Data
Dec. 23, 1985 [IT] Italy .................... 24240/85[U]
[51] Int. Cl.⁴ .................................. G01N 21/90
[52] U.S. Cl. ..................... 356/427; 422/64; 422/72
[58] Field of Search ........... 356/409, 414, 426, 427, 356/428, 436; 422/64, 72; 250/576, 236
[56] References Cited
U.S. PATENT DOCUMENTS
3,605,829  9/1971  Genese et al. ............... 422/64
4,226,531 10/1980  Tiffany et al. ............... 356/246
4,652,137  3/1987  Calzi .......................... 356/427

Primary Examiner—Eugene R. LaRoche
Assistant Examiner—David Mis
Attorney, Agent, or Firm—Alan M. Doernberg

[57] ABSTRACT

A coupling arrangement between a hub and multi-cuvette rotor in analytical photometers, wherein the hub has a projection the section of which has a non-revolving profile and to such end comprises at least one rectilinear segment, the rotor designed for said hub featuring centrally a seating adapted to receive said projection on which hub, peripherally to said projection and distanced from the rectilinear-segment portion, there are arranged radially yieldable elastic elements provided with a portion which projects from said profile so that it elastically associates with the matching seating in the rotor.

7 Claims, 9 Drawing Figures

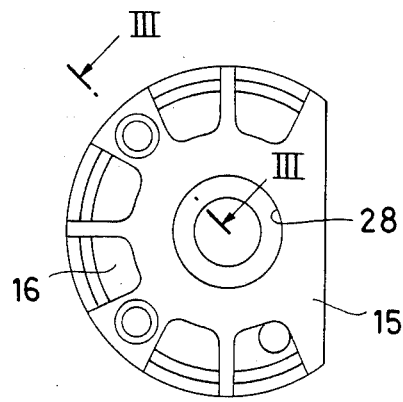
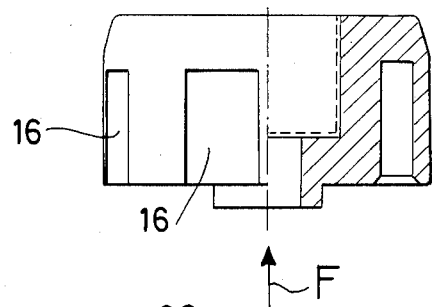
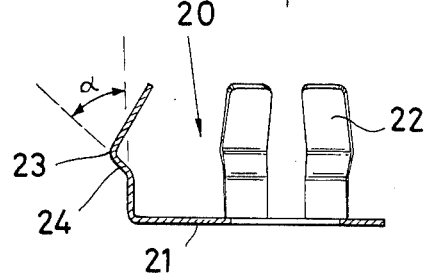
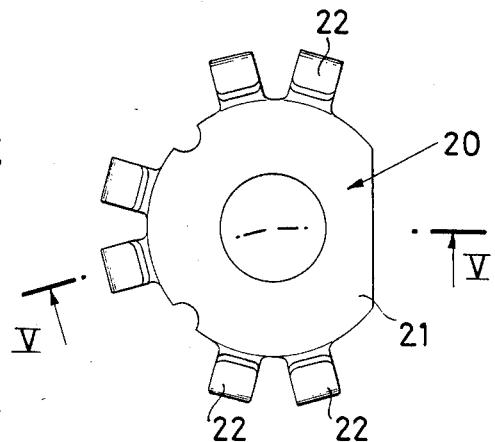

COUPLING BETWEEN ENTRAINING HUB AND MULTI-CUVETTE ROTOR FOR ANALYTICAL APPARATUS

Analytical photometers are known which provide for the use of discoid rotors constructed from plastic material of suitable characteristics, in which there are formed radially-arranged cuvettes into which the samples to be analyzed are introduced.

The cuvettes generally provide for a plurality of communicating chambers separated by dams which permit the mixing of the reagents by centrifugal force when the rotor reaches a pre-set rotational speed.

The overall structure of these multicuvette rotors is per se known and will not be further considered in detail: the functioning of the rotors and the manner in which they interact with the sensors for analyzing the samples are for example illustrated in Italian Patent Application No. 20560 A/83 of Apr. 13, 1983 of Instrumentation Laboratory S.p.A. and corresponding to U.S. Ser. No. 592,520 of Calzi, filed Mar. 23, 1984.

Rotors of this type are intended to be restrained to a hub of the analytical apparatus, so as to be rotated.

The hub is required to permit effortless and straightforward manual coupling. The coupling must also be precise both as to truing and as to angular orientation, and provide efficient retention in that all the cuvettes have to be taken in sequence proximal to the optical analysis instrument by the controlled rotation of the hub. A perfect and reproducible positional relation between the cuvette and the analytical photometer is essential if the determination is to be dependable. It has in the known art been attempted to achieve such a relation by coupling the discoid rotor to the hub by forming in the latter a circular sectioned central projection flattened laterally in a chord configuration. This projection is received by a seating in the rotor, which matches it and is thus substantially "D"-shaped, and in this manner an angularly pre-determined coupling is achieved. Again according to the known art, provision is then made for screwing into the head of the hub a knob-top screw designed to retain the rotor axially on the hub during the latter's rotation, with annular plate placed between them. It is noteworthy that during centrifugation the rotor can be affected by significant disequilibrating forces and that these cannot be eliminated merely by having due regard to the static and dynamic equilibration of the rotor. For, apart from the difficulty and cost involved in obtaining such a result on a disposable item like the rotor, the rotor itself can be disequilibrated when the samples to be analyzed are introduced into it, since these do not necessarily occupy all the cuvettes.

The configuration described above is satisfactory enough from the standpoint of ease of angular coupling of the parts; the operator can immediately and with the naked eye perceive the positional relation between the parts required for a correct coupling. However, as regards angular positional exactitude between hub and rotor, the precision of the coupling cannot be satisfactory, since the clearance, small though it may be, that must exist in the coupling if the rotor is to be placed readily on the hub and the tolerances that must be allowed for in processing—of the rotor in particular— give rise to an angular clearance between the parts which is on occasion considerable. The extent of this angular clearance in fact depends both on the differences in diameter of the projection and of the opening in the rotor, and on the tolerances between the bevel on the hub and the matching flat wall in the opening of the rotor.

Moreover, the operation of definitively securing the multicuvette rotor to the hub through the intermediary of an additional element such as the screw, is laborious.

The object of the present invention is to embody a coupling between the hub of an analytical apparatus and the multi-cuvette rotor that will ensure a precise reciprocal angular positioning of the parts, and that will also assure a satisfactory axial retention—though without calling for the use of accessory elements such as the aforesaid securing screw.

A coupling device suitable for coupling a multicuvette rotor to an analytical photometer, with the rotor having a central recess with at least one rectilinear-segment portion, comprising a hub fixedly mountable to a rotatable portion of the photometer, the hub having a projection portion shaped to have an exterior profile to fit into the central recess of the rotor and to engage the rotor at the rectilinear-segment portion, characterized by the coupling comprising in addition to the hub a plurality of elastic elements, the elastic elements projecting, in the absence of the rotor, radially outward beyond the exterior profile of the projection portion, and the elastic elements being deformed radially inward by the rotor into the exterior profile of the projection portion, with the deformed elastic elements exerting thrust radially outward against the rotor.

The object of the invention and its essential constructional characteristics will become more apparent from the following description of a practical embodiment thereof, with reference to the appended drawings in which:

FIG. 2 is a bottom view according to the arrow F of FIG. 3 of a projection designed to associate with the rotor in FIG. 1;

FIG. 3 is a partially sectional view taken on the line III—III in FIG. 2;

FIG. 4 is a plan view of an elastic unit designed to be mounted in combination with the projection in FIG. 2 as shown in FIGS. 7, 8;

FIG. 5 is a sectional view taken on the line V—V in FIG. 4;

Figure 1:
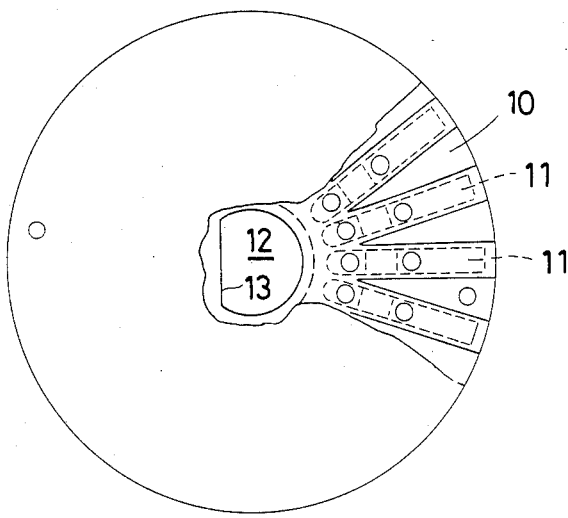
FIG. 1 is a general schematic view of a multi-cuvette rotor for which the coupling according to the invention is designed.
Figure 6:
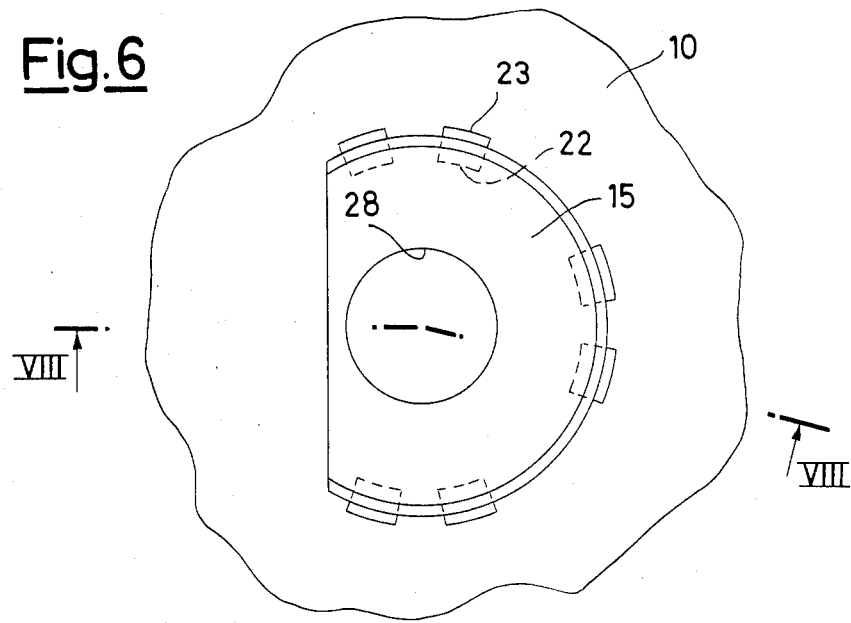
FIG. 6 is a partial schematic plan view of the coupling between hub and rotor.

As can be seen from FIG. 1, according to the present invention and in a manner per se generally known, a multicuvette rotor 10 has a discoid configuration and radially to it are formed cuvettes 11 which are intended to receive samples and reagents for the purpose of analysis. As it is known in the art and, especially, illustrated in U.S. Pat. No. 4,226,531, the particular configuration of the rotor is not here described.

In particular, the rotor has a flat central portion in which is formed a central recess or opening 12, which is generally "D"-shaped, that is to say a circular shape closed proximally to a circular segment thereof by a rectilinear base 13.

FIGS. 2–7 illustrate the characteristics of the hub on which the multicuvette rotor 10 is designed to be mounted.

Figure 7:
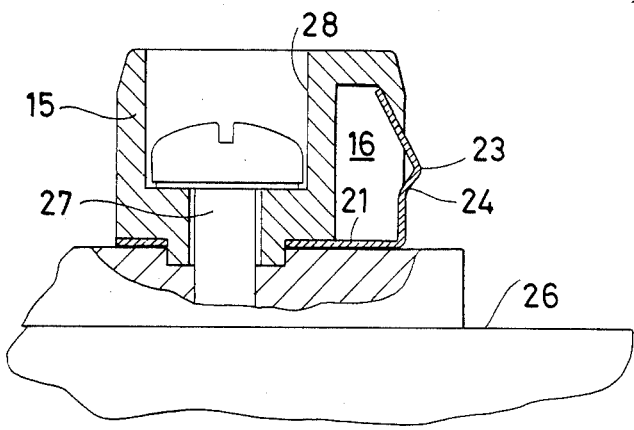
FIGS. 7 and 8 are sectional views taken on the line VIII—VIII in FIG. 6, in two different operating positions of the coupling.

The hub (FIGS. 7 and 8) comprises a central core 15 having a profile matching the profile of the opening 12, i.e. "D"-shaped. In combination with the core 15 there is mounted a locking unit for the rotor 10 better illustrated in FIG. 4 and 5 and indicated overall by 20. This locking unit 20 is composed of a stiff annular base flat portion 21 from which there peripherally depart elastically yieldable laminar elements 22 designed to be received in matching peripheral slots 16 in the core 15. Each of the elements 22 typically features a projecting portion 23 which connects with an inclined side 24 of an angled formed with the enveloping cylindrical surface of the laminas 22. The two elements 15 and 20 are designed to be mounted in combination on a rotating plate 26, as is shown in FIG. 7. In particular, a screw 27 is received by its head portion into the central seating 28 of the core 15 and, traversing the base of the latter, screws into the body of the plate 26. Pins or similar reference elements which exactly identify the mutual angular positioning of the core 15, the unit 20 and the plate 26 are not shown.

Figure 8:
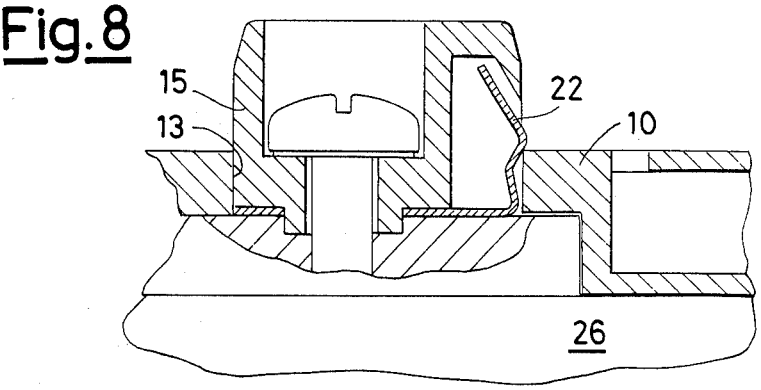

FIG. 8 illustrates how the elastically yieldable elements 22 are deformed by the positioning of the rotor 10 on the core 15, bringing to bear on the profile of the opening 12 an action of elastic support and an action of retention.

Noteworthy is the fact that each lamina 22 rests on the edge of the profile of the opening 12 with its inclined side 24, so that the thrust exerted on the rotor must be considered as having a radial component and an axial component. The overall radial component of the laminas 22 on the rotor 10 causes the thrusting of the rectilinear-segment portion or flat side 13 of the opening 12 against the matching flat side of the core 15, thus assuring the precision of the angular orientation of the rotor 10 with respect to the core 15: to this end, elastic elements 22 are not in general provided proximally to this flat side of the core (FIGS. 4, 5). The axial component exerted by the laminas on the rotor has two essential functions: firstly, it retains the rotor on the hub without any need for manually operated securing elements; secondly, the action of the elastic elements 22 elastically thrusts the rotor against the plate 26, keeping it in close contact therewith. Such a contact is of particular importance when the apparatus provides for the multicuvette rotor to be maintained at constant temperature by yielding of heat thereto by the hub, which is temperature-controlled by known heating means. It is clear that, if a good transmission is to be obtained, there must be a satisfactory contact between the parts.

In this manner the object of efficiently retaining the rotor on the hub is attained, even when pronounced centrifugation forces exist-and this, moreover, with the placing of the rotor on and its removal from the hub each being made a simple operation, such placing and removal being of latching engagement type, in view of the elasticity of the yieldable laminar elements 22 of the unit 20.

This unit 20 can be constructed from plastic material or suitable metallic material, and can have any appropriate configuration.

The unit 20 can be for instance manufactured from metallic foil, by means of blanking of a flat rough and subsequent bending and shaping of the elements 22. The kind of the metal, for instance harmonic steel or phosphor bronze, and its thickness, will be such to guarantee to the elements 22 the necessary elastic yieldability, also thanks to their laminar configuration; on the contrary, the annular base portion 21, due to its configuration and when fixed in position by screw 27, will have a substantially rigid behaviour. The unit 20 can also be produced by moulding of a suitable plastic material, for instance nylon. In this case the flat portion 21, in order to be rigid, could have stiffness ribs, while the elements 22 will have such a general configuration and dimensions to result elastically yieldable.

It is to be noted that the unit 20, described as a non-limiting example, could also be missing, because the same hub 15 could embody elastically yieldable retaining means, radially projecting from it, so to match the opening of the multicuvette rotor 10.

Figure 9:
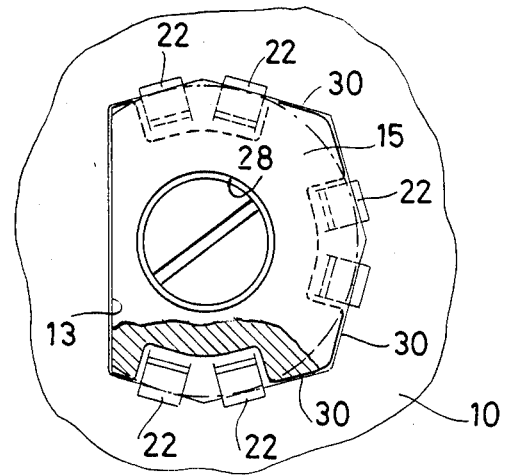
FIG. 9 is a view analogous to the view illustrated in FIG. 6, but showing a hub with poligonal profile.

The "D"-shaped section of the hub previously indicated by way of example can advantageously have a profile development of polygonal type, as is schematically shown in FIG. 9. This Figure illustrates the central opening of the core 15 in FIG. 2 replaced by a series of consecutive rectilinear sides 30. This brings the advantage that the laminas 22 can be made flat and have a correct support on a matching flat side of the central opening of the rotor. For the opening 12 of the rotor will accordingly have a polygonal profile so as to correctly match up with the periphery of the core 15 of the hub.

Although the invention has been described above in connection with one embodiment thereof, it is clear that certain modifications are possible with respect to particular applications of the invention, without thereby falling outside the scope thereof.

I claim:

1. A coupling device suitable for coupling a multicuvette rotor to an analytical photometer, with the rotor having a central recess with at least one rectilinear-segment portion, comprising a hub fixedly mountable to a rotatable portion of the photometer, the hub having a projection portion shaped to have an exterior profile to fit into the central recess of the rotor and to engage the rotor at the rectilinear-segment portion, characterized by the coupling comprising in addition to the hub a plurality of elastic elements, the elastic elements projecting, in the absence of the rotor, radially outward beyond the exterior profile of the projection portion, and the elastic elements being deformed radially inward by the rotor into the exterior profile of the projection portion, with the deformed elastic elements exerting thrust radially outward against the rotor.

2. The coupling device of claim 1 wherein the elastic elements are formed in a unitary component separate from the hub, and wherein the projection portion has an external profile corresponding to the internal profile of the central recess of the rotor and has a plurality of periphery recesses, each elastic element being partially within a peripheral recess in the absence of a rotor and being deformed further into a peripheral recess in the presence of a rotor.

3. The coupling device of claim 2 wherein the unitary component comprises an annular base portion mountable between the hub and the rotatable portion of the photometer and a plurality of elastic elements each projecting from the annular base portion into a peripheral recess in a generally axial direction.

4. The coupling device of claim 1 wherein each elastic element has an engagement surface which is tilted in the deformed position at an angle sufficient to exert thrust against the rotor at any angle to the radial direction such that the thrust has a radial component and an axial component, the axial component thrusting the rotor toward the rotatable portion of the photometer.

5. The coupling device of claim 4 wherein the elastic elements are distributed circumferentially around the hub with sufficient assymetry for the sum of the radial components of thrust to press the rotor against the hub at a rectilinear-segment portion of the central recess.

6. The coupling device of claim 1 wherein the central recess has a large rectilinear-segment portion and a plurality of small rectilinear-segment portions, and in which each elastic element engages the rotor at a small rectilinear-segment portion.

7. The coupling device of claim 4 wherein each elastic element is shaped to be deformed further radially inwardly as a rotor is being fitted onto the projection portion and to move partially radially outward once the rotor has begun clearing the inclined engagement surface.

* * * * *